(12) United States Patent
Suzuki et al.

(10) Patent No.: US 9,872,601 B2
(45) Date of Patent: Jan. 23, 2018

(54) ENDOSCOPE SYSTEM WITH ERROR OCCURRENCE PROCESSING

(71) Applicant: FUJIFILM Corporation, Tokyo (JP)

(72) Inventors: Masatoshi Suzuki, Kanagawa (JP); Koji Shimomura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 116 days.

(21) Appl. No.: 15/135,672

(22) Filed: Apr. 22, 2016

(65) Prior Publication Data
US 2016/0309983 A1 Oct. 27, 2016

(30) Foreign Application Priority Data
Apr. 24, 2015 (JP) .................. 2015-089116

(51) Int. Cl.
*A61B 1/045* (2006.01)
*A61B 1/00* (2006.01)
(Continued)

(52) U.S. Cl.
CPC ...... *A61B 1/00006* (2013.01); *A61B 1/00009* (2013.01); *A61B 1/00057* (2013.01); *A61B 1/045* (2013.01); *A61B 1/05* (2013.01); *A61B 1/0005* (2013.01); *A61B 1/00011* (2013.01); *A61B 1/00025* (2013.01);
(Continued)

(58) Field of Classification Search
CPC ............ A61B 1/00006; A61B 1/00009; A61B 1/00011; A61B 1/00025; A61B 1/045; A61B 1/05; H04N 2005/2255; H04N 5/3698
See application file for complete search history.

(56) References Cited

U.S. PATENT DOCUMENTS

2009/0058997 A1\* 3/2009 Kato ............... H04N 7/183
348/65
2011/0242300 A1 10/2011 Hashimoto
(Continued)

FOREIGN PATENT DOCUMENTS

| JP | 2011-206335 A | 10/2011 |
|---|---|---|
| JP | 2013-172904 A | 9/2013 |

OTHER PUBLICATIONS

Extended European Search Report, dated Jul. 8, 2016, for European Application No. 16166424.8.

*Primary Examiner* — John P Leubecker
(74) *Attorney, Agent, or Firm* — Birch, Stewart, Kolasch & Birch, LLP (57) ABSTRACT

An endoscope system includes: an electronic endoscope having an imaging device and a first processing unit which judges whether a first error has occurred that is an error in image data taken by the imaging device and resets the imaging device if a variable for judgment of occurrence of a first error is larger than or equal to a first threshold value; a light source unit which supplies illumination light to the electronic endoscope, and a second processing unit which judges whether a second error has occurred that is an error in image data transmitted from the electronic endoscope and initializes supply of power to the electronic endoscope if a variable for judgment of occurrence of a second error is larger than or equal to a second threshold value that is larger than or equal to the first threshold value; and a processor as defined herein.

13 Claims, 4 Drawing Sheets

(51) Int. Cl.
    *A61B 1/05*         (2006.01)
    *A61B 1/04*         (2006.01)
    *A61B 1/06*         (2006.01)
    *G02B 23/24*       (2006.01)
    *H04N 5/225*      (2006.01)

(52) U.S. Cl.
    CPC ............ *A61B 1/042* (2013.01); *A61B 1/0669* (2013.01); *G02B 23/2476* (2013.01); *H04N 2005/2255* (2013.01)

(56) References Cited

U.S. PATENT DOCUMENTS

| | | | |
|---|---|---|---|
| 2013/0169775 A1* | 7/2013 | Ono | A61B 1/00009 348/68 |
| 2013/0176410 A1* | 7/2013 | Takahashi | A61B 1/045 348/65 |
| 2014/0340496 A1* | 11/2014 | Okawa | A61B 1/00006 348/65 |
| 2015/0374204 A1* | 12/2015 | Tabuchi | A61B 1/04 600/109 |
| 2016/0241647 A1* | 8/2016 | Kasumi | G06T 7/0002 |
| 2016/0248974 A1* | 8/2016 | Tabuchi | G02B 23/2476 |
| 2017/0095137 A1* | 4/2017 | Kinouchi | A61B 1/04 |

\* cited by examiner

ENDOSCOPE SYSTEM WITH ERROR OCCURRENCE PROCESSING

CROSS-REFERENCE TO RELATED APPLICATIONS

This application claims the benefit of Japanese Patent Application JP 2015-089116, filed Apr. 24, 2015, the entire content of which is hereby incorporated by reference, the same as if set forth at length.

FIELD OF THE INVENTION

The present invention relates to an endoscope system.

BACKGROUND OF THE INVENTION

Endoscope systems to be used for medical diagnoses etc. are composed of an electronic endoscope to be inserted into the body cavity of a subject, a light source unit for generating light for illuminating the inside of a body cavity being guided by a light guide provided inside the electronic endoscope, and a processor for performing image processing on an imaging signal that is output from a solid-state imaging device installed in the electronic endoscope and outputting a resulting observation image to a monitor.

JP-A-2011-206335 discloses an endoscope system that can be restored to a normal state as quickly as possible when a CMOS imaging device provided in an endoscope device has been rendered uncontrollable. In this endoscope system, when the CMOS imaging device been rendered uncontrollable, first, a soft reset is done to initialize a register of the CMOS imaging device. If recovery to a normal state is not made, a device reset of the CMOS imaging device is done. If recovery to a normal state is not attained even by the device reset, the supply of power to the CMOS imaging device is suspended temporarily and then restarted.

JP-A-2013-172904 discloses an endoscope system which can determine an abnormality location in an endoscope in a detailed manner. The endoscope is equipped with a sensor unit, an AFE unit for performing signal processing on a signal that includes image information that is output from the sensor unit, and a P/S conversion unit for sending a signal thus produced by the AFE unit to the outside. Each unit generates a judgment signal to be used for judgment of its own operation state. The endoscope is also equipped with an abnormality judging unit capable of judging occurrence/non-occurrence of an abnormality in the sensor unit, the AFE unit, and the P/S conversion unit individually on the basis of the above judgment signals and a reset control unit for resetting, independently, the operation of a location where the abnormality judging unit has found an abnormality.

SUMMARY OF THE INVENTION

In the above endoscope system disclosed in JP-A-2011-206335, the method for resetting the CMOS imaging device rendered uncontrollable is changed step by step. Although the CMOS imaging device can be recovered to a normal state quickly by resetting it step by step, only the criterion for doing a reset is whether the CMOS imaging device is uncontrollable or not. Furthermore, in this endoscope system, for example, an imaging signal that is output from the CMOS imaging device is not reset according to a location where an error has occurred.

In the above endoscope disclosed in JP-A-2013-172904, the sensor unit, the AFE unit, and the P/S conversion unit generate respective judgment signals and the abnormality judging unit judges, individually, on the basis of the judgment signals, whether an abnormality has occurred in the sensor unit, the AFE unit, and the P/S conversion unit. Furthermore, since the abnormality judging unit resets, independently, a location where an abnormality has occurred, the time to recover from the abnormal state can be shortened. However, a common resetting method is employed irrespective of the abnormality location. Therefore, the time to recover from an abnormal state does not vary as long as what is to be reset (abnormal location) is the same.

The present invention has been made in the above circumstances, and an object of the invention is therefore to provide an endoscope system capable of shortening times of recovery to a normal state for errors occurring at different locations.

An endoscope system of an embodiment of the invention comprises: an electronic endoscope having an imaging device and a first processing unit which judges whether a first error has occurred that is an error in image data taken by the imaging device and resets the imaging device if a variable for judgment of occurrence of a first error is larger than or equal to a first threshold value; a light source unit which supplies illumination light to the electronic endoscope, and a second processing unit which judges whether a second error has occurred that is an error in image data transmitted from the electronic endoscope and initializes supply of power to the electronic endoscope if a variable for judgment of occurrence of a second error is larger than or equal to a second threshold value that is larger than or equal to the first threshold value; and a processor having a third processing unit which performs image processing on image data transmitted from the electronic endoscope via the light source unit.

The invention can provide an endoscope system capable of shortening times of recovery to a normal state for errors occurring at different locations.

DESCRIPTION OF SYMBOLS

10: Endoscope system
11: Electronic endoscope
12: Light source unit
13: Processor
14: Insertion unit
15: Manipulation unit
16: Connector
17: Universal cord
18: Monitor
111: Imaging device
112: First processing unit
113: Image data sending unit
114: Secondary coil
115: Signal communication unit
116: Switch 121: Image data receiving unit
122: Second processing unit
123: Image data sending unit
124: Primary coil
125: First signal communication unit
126: Second signal communication unit
131: Image data receiving unit
132: Third processing unit
133: Signal communication unit
134: Display processing unit

DETAILED DESCRIPTION OF THE INVENTION

An embodiment of the present invention will be hereinafter described with reference to the drawings.

Figure 1:
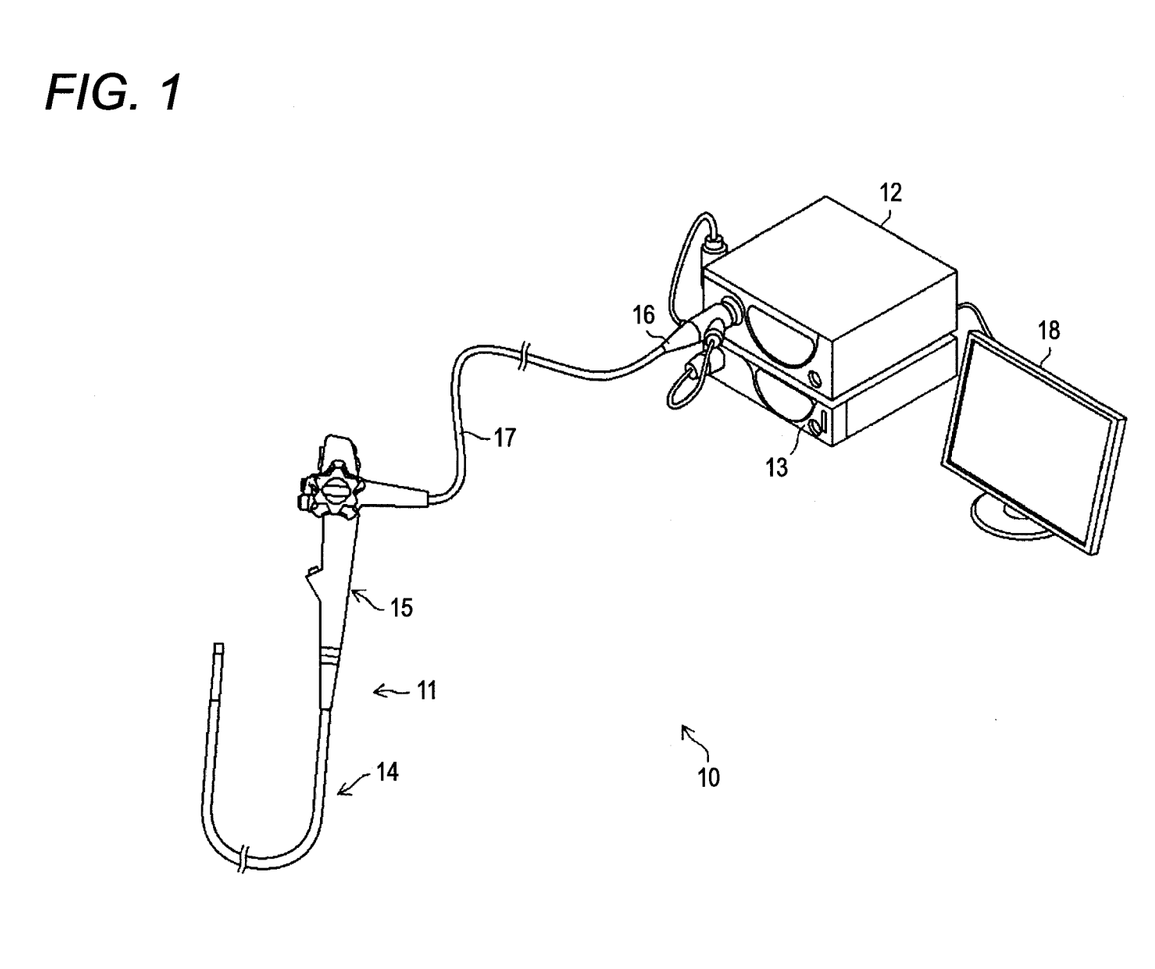
FIG. 1 shows an appearance of an endoscope system according to an embodiment of the present invention.

FIG. 1 shows an appearance of an endoscope system 10 according to the embodiment of the invention. As shown in FIG. 1, the endoscope system 10 is equipped with an electronic endoscope 11, a light source unit 12, a processor 13 which is electrically connected to the electronic endoscope 11 and the light source unit 12, and a monitor 18.

The electronic endoscope 11 has a flexible insertion unit 14 to be inserted into the body cavity of a subject, a manipulation unit 15 which is continuous with a proximal portion of the insertion unit 14, a connector 16 which is connected to the light source unit 12 and the processor 13, and a universal cord 17 which connects the manipulation unit 15 and the connector 16. An imaging device such as a CCD (charge-coupled device) or a CMOS (complementary metal-oxide-semiconductor) sensor for converting an optical signal into an imaging signal through photoelectric conversion is installed inside a tip portion of the insertion unit 14. Image data taken by the imaging device is transmitted from the electronic endoscope 11 to the light source unit 12.

The light source unit 12 supplies the electronic endoscope 11 with illumination light for illuminating an observation region through an illumination window that is formed in a tip surface of the electronic endoscope 11. Illumination light that is supplied from the light source unit 12 is transmitted to the tip surface of a tip hard portion of the electronic endoscope 11 via the universal cord 17 and a light guide (not shown) that is a bundle of a number of optical fibers and is inserted in the insertion unit 14. The light source unit 12 sends, to the processor 13, image data that is transmitted from the electronic endoscope 11. Furthermore, the light source unit 12 supplies power to the electronic endoscope 11 by electromagnetic induction.

The processor 13 performs various kinds of image processing on image data that is transmitted from the light source unit 12, and thereby convers the image data into a video signal. The video signal thus produced by the processor 13 is displayed as an observation image on the monitor 18 which is connected to the processor 13. The processor 13 sends a control signal for controlling the electronic endoscope 11 and other signals to the electronic endoscope 11 via the light source unit 12.

Figure 2:
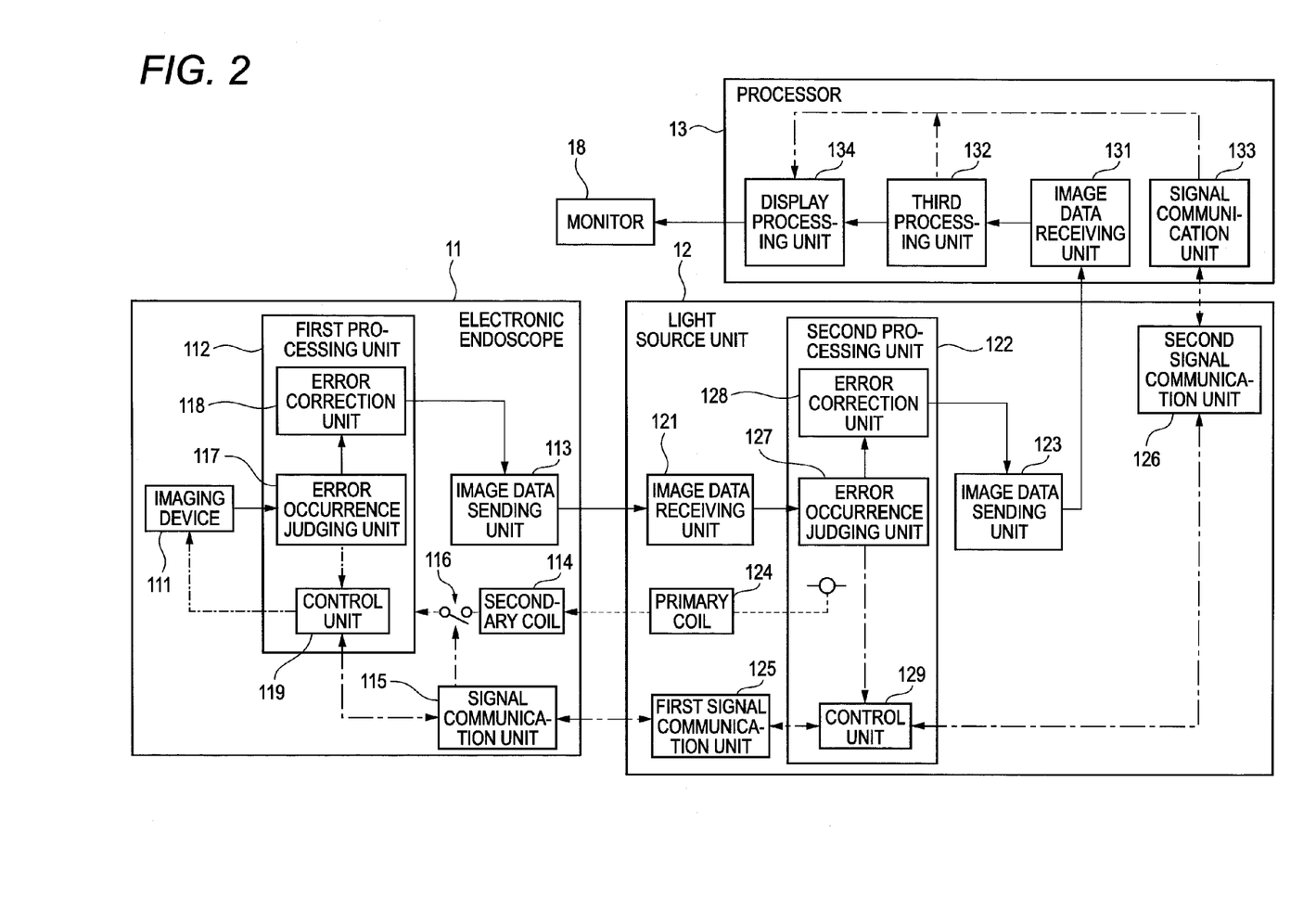
FIG. 2 is a block diagram showing the configuration of a control system of the endoscope system shown in FIG. 1.

FIG. 2 is a block diagram showing the configuration of a control system of the endoscope system 10 shown in FIG. 1. In FIG. 2, solid-line arrows, broken-line arrows, and chain-line arrows indicate transmission of image data, energy, and signals or notices, respectively.

As shown in FIG. 2, the electronic endoscope 11 has an imaging device 111, a first processing unit 112, an image data sending unit 113, a secondary coil 114, a signal communication unit 115, and a switch 116. The light source unit 12 has an image data receiving unit 121, a second processing unit 122, an image data sending unit 123, a primary coil 124, a first signal communication unit 125, and a second signal communication unit 126. The processor 13 has an image data receiving unit 131, a third processing unit 132, and a signal communication unit 133, and a display processing unit 134.

The individual components of the electronic endoscope 11 will be described below. The imaging device 111 of the electronic endoscope 11 is a CCD (charge-coupled device) or a CMOS (complementary metal-oxide-semiconductor) sensor for converting an optical image into an imaging signal through photoelectric conversion.

The first processing unit 112 has an error occurrence judging unit 117, an error correction unit 118, and a control unit 119. The error occurrence judging unit 117 judges, using first threshold values th01, whether a first error that is an error in image data taken by the imaging device 111 has occurred or not. The first threshold values th01 (the numbers of errors occurring consecutively) are "10" for frame errors in image data and "1,000" for line errors in image data. Therefore, the error occurrence judging unit 117 judges that a first error has occurred if frame errors have occurred 10 times consecutively in image data or line errors have occurred 1,0000 times consecutively in image data. The error correction unit 118 corrects the errors in the image data and sends the corrected image data to the image data sending unit 113.

If the error occurrence judging unit 117 judges that a first error has occurred, the control unit 119 resets the imaging device 111. The control unit 119 counts the number of times of occurrence of a first error. If the cumulative number of times of occurrence of a first error (first error occurrence cumulative number) has become larger than or equal to a first prescribed value th11, the control unit 119 outputs a first error occurrence notice to be sent to the processor 13 via the light source unit 12. The first error occurrence notice indicates that errors have occurred frequently in the electronic endoscope 11. Upon outputting the first error occurrence notice, the control unit 119 returns the first error occurrence cumulative number to "0."

The image data sending unit 113 sends, to the light source unit 12, the image data taken by the imaging device 111 or the data error-corrected by the error correction unit 118. The transmission of (corrected) image data from the image data sending unit 113 may be either wireless or wire transmission of an electrical signal or transmission of an optical signal.

The secondary coil 114 converts electromagnetic energy that is transmitted from the primary coil 124 (described later) of the light source unit 12 by electromagnetic induction into electric energy. The power obtained by the secondary coil 114 is supplied to the individual components, such as the first processing unit 112, of the electronic endoscope 11.

The signal communication unit 115 receives a signal transmitted from the first signal communication unit 125 (described later) of the light source unit 12. If receiving a signal that commands initialization of power supply to the electronic endoscope 11, the signal communication unit 115 off-controls the switch 116 and then on-controls it after a lapse of a prescribed time. If the switch 116 is off-controlled and on-controlled, the power supply to the individual components of the electronic endoscope 11 is initialized. The signal communication unit 115 sends, to the light source unit 12, a first error occurrence notice that is output from the control unit 119. The transmission of a signal to/from the signal communication unit 115 may be either wireless or wire transmission of an electrical signal or transmission of an optical signal.

Next, the individual components of the light source unit 12 will be described. The image data receiving unit 121 of the light source unit 12 receives image data that is transmitted from the electronic endoscope 11. The transmission of data to the image data receiving unit 121 may be either wireless or wire transmission of an electrical signal or transmission of an optical signal.

The second processing unit 122 has an error occurrence judging unit 127, an error correction unit 128, and a control unit 129. The error occurrence judging unit 127 judges, using second threshold values th02, whether a second error that is an error in image data transmitted from the electronic endoscope 11 has occurred or not. The second threshold values th02 (the numbers of errors occurring consecutively) are "100" for frame errors in image data and "10,000" for line errors in image data. Therefore, the error occurrence judging unit 127 judges that a second error has occurred if frame errors have occurred 100 times consecutively in image data or line errors have occurred 10,0000 times consecutively in image data. The error correction unit 128 corrects the errors in the image data and sends the corrected image data to the image data sending unit 123.

If the error occurrence judging unit 127 judges that a second error has occurred, the control unit 129 outputs, to the first signal communication unit 125, a signal that commands initialization of power supply to the electronic endoscope 11. Furthermore, the control unit 119 counts the number of times of occurrence of a second error. If the cumulative number of times of occurrence of a second error (second error occurrence cumulative number) has become larger than or equal to a second prescribed value th12, the control unit 129 outputs a second error occurrence notice to be sent to the processor 13. The second error occurrence notice indicates that errors have occurred frequently during transmission of image data from the electronic endoscope 11 to the light source unit 12. Upon outputting the second error occurrence notice, the control unit 129 returns the second error occurrence cumulative number to "0."

The image data sending unit 123 sends, to the processor 13, the image data transmitted from the electronic endoscope 11 or the data error-corrected by the error correction unit 128.

To supply power to the electronic endoscope 11 through electromagnetic induction, the primary coil 124 sends electromagnetic energy to the secondary coil 114 of the imaging device 111.

The first signal communication unit 125 sends, to the electronic endoscope 11, a signal received from the control unit 129. And the first signal communication unit 125 receives a first error occurrence notice that is transmitted from the electronic endoscope 11. The transmission of a signal to/from the first signal communication unit 125 may be either wireless or wire transmission of an electrical signal or transmission of an optical signal.

The second signal communication unit 126 receives a signal that is transmitted from the signal communication unit 133 (described later) of the processor 13, and sends the received signal to the control unit 129. Furthermore, the second signal communication unit 126 sends, to the processor 13, a second error occurrence notice that is output from the control unit 129 and/or a first error occurrence notice that is received by the first signal communication unit 125.

Next, the individual components of the processor 13 will be described. The image data receiving unit 131 of the processor 13 receives image data that is transmitted from the light source unit 12.

The third processing unit 132 performs image processing on image data that is received by the image data receiving unit 131. The third processing unit 132 judges, using third threshold values th03, whether a third error that is an error in image data transmitted from the light source unit 12 has occurred or not. The third threshold value th03 (the numbers of errors occurring consecutively) are "200" for frame errors in image data and "20,000" for line errors in image data. Therefore, the third processing unit 132 judges that a third error has occurred if frame errors have occurred 200 times consecutively in image data or line errors have occurred 20,0000 times consecutively in image data.

The signal communication unit 133 sends, to the light source unit 12, signals relating to the control etc. of the electronic endoscope 11 and the light source unit 12. Furthermore, the signal communication unit 133 receives a first error occurrence notice and/or second error occurrence notice from the light source unit 12. The received first error occurrence notice and/or second error occurrence notice is sent to the display processing unit 134.

The display processing unit 134 processes the video of image data that has been processed by the third processing unit 132, to make it suitable for display by the monitor 18. Furthermore, the display processing unit 134 processes error information including information of an error occurrence location(s) that corresponds to an error occurrence notice received by the signal communication unit 133 and/or a third error determined by the third processing unit 132, to make it suitable for display by the monitor 18. When error information that is based on a first error occurrence notice is displayed on the monitor 18, it indicates that an error has occurred in the electronic endoscope 11, particularly in the imaging device 111. When error information that is based on a second error occurrence notice is displayed on the monitor 18, it indicates that an error has occurred on the transmission path between the electronic endoscope 11 and the light source unit 12. When error information that is based on a third error is displayed on the monitor 18, it indicates that an error has occurred on the transmission path between the light source unit 12 and the processor 13.

Figure 3:
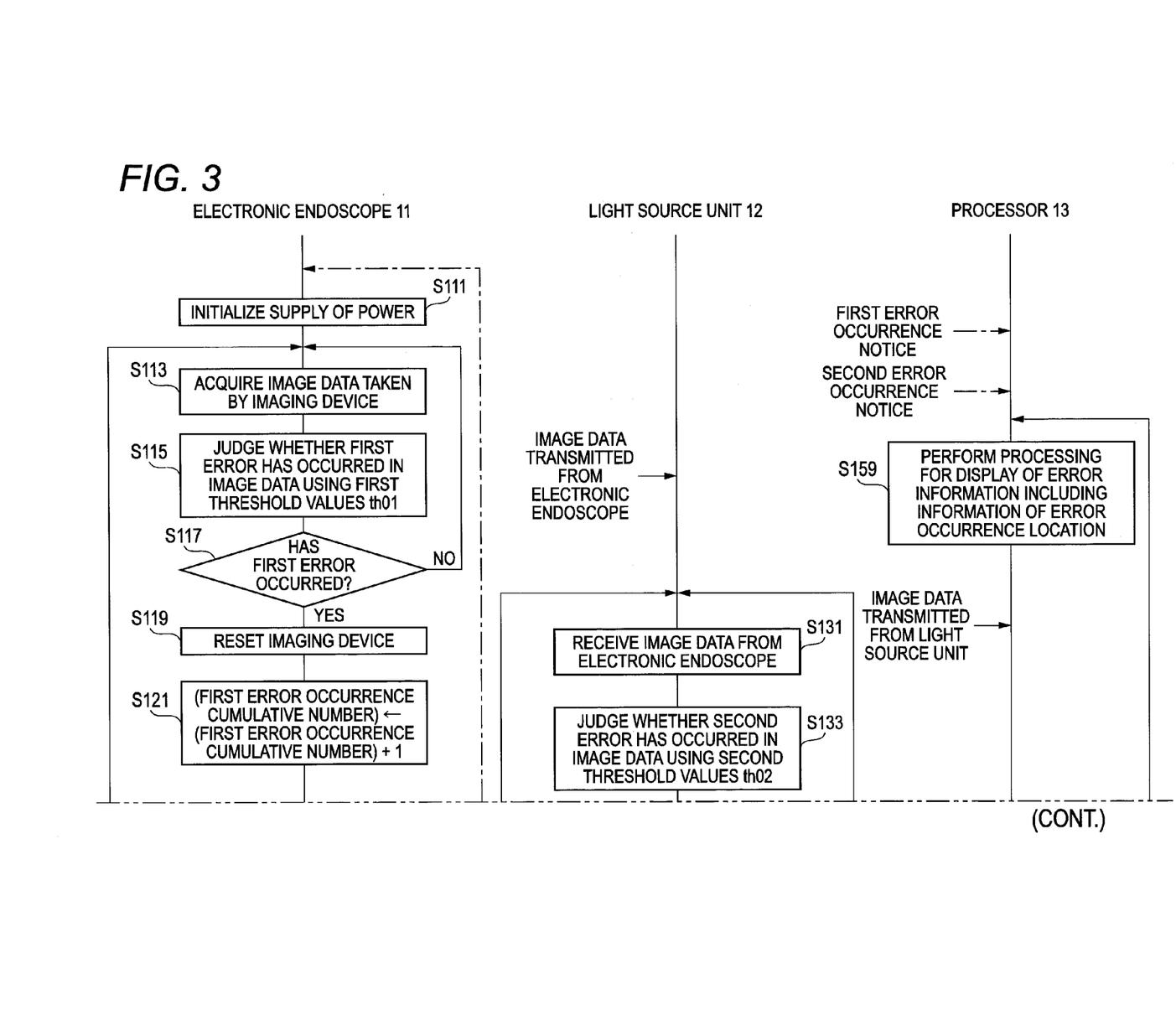
FIG. 3 is a flowchart showing how the control system of the endoscope system shown in FIG. 1 operates.

Next, a description will be made of how the endoscope system 10 having the above-described control system operates. FIG. 3 is a flowchart showing how the control system of the endoscope system 10 according to the embodiment operates. Processes that are executed by the electronic endoscope 11, the light source unit 12, and the processor 13 will described below separately.

[Operation of Electronic Endoscope 11]

As shown in FIG. 3, in the electronic endoscope 11, the supply of power to the electronic endoscope 11 is initialized at step S111, whereupon at step S113 the first processing unit 112 of the electronic endoscope 11 acquires image data taken by the imaging device 111. At steps S115 and S117, the error occurrence judging unit 117 judges whether or not a first error that is an error in the image data taken by the imaging device 111 has occurred using the first threshold values th01 ("10" (errors occurring consecutively) for frame errors in image data and "1,000" (errors occurring consecutively) for line errors in image data). If it is judged at step S117 that a first error has occurred, the process moves to step S119. The process returns to step S113 if it is judged at step S117 that no first error has occurred.

At step S119, the control unit 119 of the electronic endoscope 11 resets the imaging device 111. At step S121, the control unit 119 increments the first error occurrence cumulative number. At step S123, the control unit 119 judges whether or not the first error occurrence cumulative number is larger than or equal to the first prescribed value th11. If it is judged at step S123 that the first error occurrence cumulative number is larger than or equal to the first prescribed value th11, the process moves to step S125. The process returns to step S113 if (first error occurrence cumulative number)<th11.

At step S125, the signal communication unit 115 sends the first error occurrence notice that is output from the control unit 119 of the electronic endoscope 11, to the processor 13 via the light source unit 12. At step S127, the control unit 119 returns the first error occurrence cumulative number to "0." Then the process returns to step S113.

[Operation of Light Source Unit 12]

In the light source unit 12, at step S131 the image data receiving unit 121 receives image data from the electronic endoscope 11. At steps S133 and S135, the error occurrence judging unit 127 judges whether or not a second error that is an error in the image data transmitted from the electronic endoscope 11 has occurred using the second threshold values th02 ("100" (errors occurring consecutively) for frame errors in image data and "10,000" (errors occurring consecutively) for line errors in image data). If it is judged at step S135 that a second error has occurred, the process moves to step S137. The process returns to step S131 if it is judged at step S135 that no second error has occurred.

At step S137, the control unit 129 of the light source unit 12 increments the second error occurrence cumulative number. At step S139, the control unit 129 judges whether or not the second error occurrence cumulative number is larger than or equal to the second prescribed value th12. If it is judged at step S139 that the second error occurrence cumulative number is larger than or equal to the second prescribed value th12, the process moves to step S141. The process returns to step S131 if (second error occurrence cumulative number)<th12.

At step S141, the control unit 129 of the light source unit 12 outputs a signal that commands initialization of the power supply to the electronic endoscope 11 and the first signal communication unit 125 sends this initialization command signal to the electronic endoscope 11. In the electronic endoscope 11 that has received the initialization command signal, the switch 116 is off-controlled and then on-controlled, whereby the supply of power to the individual components of the electronic endoscope 11 is initialized.

At step S143, the second signal communication unit 126 sends, to the processor 13, a second error occurrence notice that is output from the control unit 129 of the light source unit 12. At step S145, the control unit 129 returns the second error occurrence cumulative number to "0." Then the process returns to step S131.

[Operation of Processor 13]

In the processor 13, at step S151 the image data receiving unit 131 receives image data from the light source unit 12. At steps S153 and S155, the third processing unit 132 judges whether or not a third error that is an error in the image data transmitted from the light source unit 12 has occurred using the third threshold values th03 ("200" (errors occurring consecutively) for frame errors in image data and "20,000" (errors occurring consecutively) for line errors in image data). If it is judged at step S155 that a third error has occurred, the process moves to step S159. The process moves to step S157 if it is judged at step S155 that no third error has occurred.

At step S157, the third processing unit 132 performs image processing on the image data and the display processing unit 134 processes the video of the resulting image data to display it on the monitor 18. At step S159, the display processing unit 134 processes error information including information of an error occurrence location(s) that corresponds to a first error occurrence notice transmitted from the electronic endoscope 11, a second error occurrence notice transmitted from the light source unit 12, and/or a third error determined by the third processing unit 132 at step S155, to display it on the monitor 18. Step S159 is executed when the processor 13 receives a first error occurrence notice or a second error occurrence notice, irrespective of occurrence/non-occurrence of a third error.

As described above, in the embodiment, if a first error has occurred in image data taken by the imaging device 111 of the electronic endoscope 11, the imaging device 111 is reset. If a second error has occurred in image data transmitted from the electronic endoscope 11 to the light source unit 12, the supply of power to the electronic endoscope 11 is initialized. The time from a reset of the electronic endoscope 11 to a time point when the electronic endoscope 11 becomes usable is shorter than the time from a reset of the supply of power to the electronic endoscope 11 to a time point when the electronic endoscope 11 becomes usable. Therefore, when a first error has occurred in the electronic endoscope 11, the electronic endoscope 11 can be restored to a normal state in a shorter time than in a case of a second error occurring during transmission of image data to the light source unit 12.

In the embodiment, the first threshold values th01 ("10" (errors occurring consecutively) for frame errors in image data and "1,000" (errors occurring consecutively) for line errors in image data) are smaller than the respective second threshold values th01 ("100" (errors occurring consecutively) for frame errors in image data and "10,000" (errors occurring consecutively) for line errors in image data). Therefore, the judgment sensitivity for a first error to occur in the electronic endoscope 11 is higher than that for a second error to occur during transmission of image data from the electronic endoscope 11 to the light source unit 12. Since as mentioned above the recovery time of the electronic endoscope 11 from a first error for which the judgment sensitivity is high is longer than that from a second error for which the judgment sensitivity is low, the levels of the judgment sensitivities for the different kinds of errors are well balanced with the lengths of the times it takes the electronic endoscope 11 to recover.

Furthermore, in the embodiment, the processor 13 performs processing for causing the monitor 18 to display error information including information of an error occurrence location(s) that corresponds to a first error occurrence notice transmitted from the electronic endoscope 11, a second error occurrence notice transmitted from the light source unit 12, and/or a third error determined by the processor 13. Showing where an error has occurred in the endoscope system 10 in this manner makes it possible to urge a user to take a measure against it.

An described above, an endoscope system disclosed in this specification comprises an electronic endoscope having an imaging device and a first processing unit which judges whether a first error has occurred that is an error in image data taken by the imaging device and resets the imaging device if a variable for judgment of occurrence of a first error is larger than or equal to a first threshold value; a light source unit which supplies illumination light to the electronic endoscope, and a second processing unit which judges whether a second error has occurred that is an error in image data transmitted from the electronic endoscope and initializes supply of power to the electronic endoscope if a variable for judgment of occurrence of a second error is larger than or equal to a second threshold value that is larger than or equal to the first threshold value; and a processor having a third processing unit which performs image processing on image data transmitted from the electronic endoscope via the light source unit.

If a first error occurrence cumulative number is larger than or equal to a first prescribed value, the first processing unit sends a first error occurrence notice to the processor via the error correction unit.

If a second error occurrence cumulative number is larger than or equal to a second prescribed value, the second processing unit sends a second error occurrence notice to the processor.

The third processing unit processes error information including information of an error occurrence location corresponding to an error occurrence notice received by the processor to make the error information suitable for display by a monitor.

If the processor receives the first error occurrence notice, the third processing unit processes error information so that a fact that an error has occurred in the imaging device is displayed on the monitor as part of the error information. If the processor receives the second error occurrence notice, the third processing unit processes error information so that a fact that an error has occurred on a path between the electronic endoscope and the light source unit is displayed on the monitor as part of the error information.

The third processing unit judges whether a third error has occurred that is an error in image data transmitted from the light source unit. If judging that a third error has occurred, the third processing unit processes error information so that a fact that an error has occurred on a path between the light source unit and the processor is displayed on the monitor as part of the error information.

What is claimed is:

1. An endoscope system comprising:
   an electronic endoscope having an imaging device and a first processing unit which judges whether a first error has occurred that is an error in image data taken by the imaging device and resets the imaging device if a variable for judgment of occurrence of a first error is larger than or equal to a first threshold value;
   a light source unit which supplies illumination light to the electronic endoscope, and a second processing unit which judges whether a second error has occurred that is an error in image data transmitted from the electronic endoscope and initializes supply of power to the electronic endoscope if a variable for judgment of occurrence of a second error is larger than or equal to a second threshold value that is larger than or equal to the first threshold value; and
   a processor having a third processing unit which performs image processing on image data transmitted from the electronic endoscope via the light source unit.

2. The endoscope system according to claim 1, wherein if a first error occurrence cumulative number is larger than or equal to a first prescribed value, the first processing unit sends a first error occurrence notice to the processor via the error correction unit.

3. The endoscope system according to claim 2, wherein if a second error occurrence cumulative number is larger than or equal to a second prescribed value, the second processing unit sends a second error occurrence notice to the processor.

4. The endoscope system according to claim 3, wherein the third processing unit processes error information including information of an error occurrence location corresponding to an error occurrence notice received by the processor to make the error information suitable for display by a monitor.

5. The endoscope system according to claim 4, wherein if the processor receives the first error occurrence notice the third processing unit processes error information so that a fact that an error has occurred in the imaging device is displayed on the monitor as part of the error information, and if the processor receives the second error occurrence notice the third processing unit processes error information so that a fact that an error has occurred on a path between the electronic endoscope and the light source unit is displayed on the monitor as part of the error information.

6. The endoscope system according to claim 5, wherein the third processing unit judges whether a third error has occurred that is an error in image data transmitted from the light source unit, and if judging that a third error has occurred, the third processing unit processes error information so that a fact that an error has occurred on a path between the light source unit and the processor is displayed on the monitor as part of the error information.

7. The endoscope system according to claim 2, wherein the third processing unit processes error information including information of an error occurrence location corresponding to an error occurrence notice received by the processor to make the error information suitable for display by a monitor.

8. The endoscope system according to claim 7, wherein if the processor receives the first error occurrence notice the third processing unit processes error information so that a fact that an error has occurred in the imaging device is displayed on the monitor as part of the error information, and if the processor receives the second error occurrence notice the third processing unit processes error information so that a fact that an error has occurred on a path between the electronic endoscope and the light source unit is displayed on the monitor as part of the error information.

9. The endoscope system according to claim 8, wherein the third processing unit judges whether a third error has occurred that is an error in image data transmitted from the light source unit, and if judging that a third error has occurred, the third processing unit processes error information so that a fact that an error has occurred on a path between the light source unit and the processor is displayed on the monitor as part of the error information.

10. The endoscope system according to claim 1, wherein if a second error occurrence cumulative number is larger than or equal to a second prescribed value, the second processing unit sends a second error occurrence notice to the processor.

11. The endoscope system according to claim 10, wherein the third processing unit processes error information including information of an error occurrence location corresponding to an error occurrence notice received by the processor to make the error information suitable for display by a monitor.

12. The endoscope system according to claim 11, wherein if the processor receives the first error occurrence notice the third processing unit processes error information so that a fact that an error has occurred in the imaging device is displayed on the monitor as part of the error information, and if the processor receives the second error occurrence notice the third processing unit processes error information so that a fact that an error has occurred on a path between the electronic endoscope and the light source unit is displayed on the monitor as part of the error information.

13. The endoscope system according to claim 12, wherein the third processing unit judges whether a third error has occurred that is an error in image data transmitted from the light source unit, and if judging that a third error has occurred, the third processing unit processes error information so that a fact that an error has occurred on a path between the light source unit and the processor is displayed on the monitor as part of the error information.

\* \* \* \* \*